US00PP12849P2

(12) United States Plant Patent
Fruehwirth

(10) Patent No.: US PP12,849 P2
(45) Date of Patent: Aug. 13, 2002

(54) POINSETTIA PLANT NAMED 'ECKADIN'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 55 days.

(21) Appl. No.: 09/779,343

(22) Filed: Feb. 9, 2001

(51) Int. Cl.[7] ..... A01H 5/00
(52) U.S. Cl. ..... Plt./307
(58) Field of Search ..... Plt./307

*Primary Examiner*—Bruce R. Campell
*Assistant Examiner*—A Para
(74) *Attorney, Agent, or Firm*—C. A. Whealy

(57) ABSTRACT

A new and distinct cultivar of Poinsettia plant named 'Eckadin', characterized by its large inflorescences with bright red-colored flower bracts; dark green-colored leaves with burgundy-colored petioles; compact, uniform and upright plant habit; very freely branching habit; natural season flower maturity date is November 28 for plants grown in Encinitas, Calif., response time, about 9 weeks; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Eckadin'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia originated from a cross made by the Inventor of the Poinsettia cultivar 603, disclosed in U.S. Plant Pat. No. 9,952, as the female, or seed, parent, with a proprietary Poinsettia selection identified as F-14, not patented, as the male, or pollen, parent. The cultivar Eckadin was discovered and selected by the Inventor as a flowering plant within the progeny of the stated cross in a controlled environment in Encinitas, Calif., in December, 1996. The selection of this plant was based on its attractive flower bract colors and good plant form and substance.

Asexual reproduction of the new Poinsettia by terminal cuttings taken at Encinitas, Calif., since 1997, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadin'. These characteristics in combination distinguish 'Eckadin' as a new and distinct cultivar.

1. Large inflorescences with bright red-colored flower bracts.

2. Dark green-colored leaves with burgundy-colored petioles.

3. Compact, uniform and upright plant habit.

4. Very freely branching habit.

5. Natural season flower maturity date is November 28 for plants grown in Encinitas. Calif.; response time, about 9 weeks.

6. Excellent post-production longevity.

Compared to plants of the female parent, the cultivar 603, plants of the new Poinsettia are taller and have more cyathia per inflorescence. Compared to plants of the male parent, the selection F-14, plants of the new Poinsettia differ in flower bract coloration and are more freely branching and not as vigorous.

Plants of the new Poinsettia can be compared to plants of the Poinsettia cultivar Pepride, disclosed in U.S. Plant Pat. No. 10,183. In side-by-side comparisons conducted in Encinitas, Calif., plants of the new Poinsettia differed from plants of the cultivar Pepride in the following characteristics:

1. Plants of the new Poinsettia are more upright and taller than plants of the cultivar Pepride.

2. Plants of the new Poinsettia have larger leaves than plants of the cultivar Pepride. In addition, leaves of the new Poinsettia are mostly ovate in shape with occasional lobing whereas leaves of the cultivar Pepride are distinctly lobed.

3. Plants of the new Poinsettia have larger inflorescences with larger flower bracts than plants of the cultivar Pepride. In addition, flower bracts of the new Poinsettia are mostly ovate in shape with occasional lobing whereas flower bracts of the cultivar Pepride are distinctly lobed.

4. Plants of the new Poinsettia have larger cyathia clusters than plants of the cultivar Pepride.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical plant of 'Eckadin'.

The photograph at the top of the second sheet comprises a top perspective view of a typical plant of 'Eckadin'.

The photograph at the bottom of the second sheet is a close-up view of typical leaves and flower bracts of 'Eckadin' (top) and 'Pepride' (bottom). Plants used in the photographs were about 18 weeks old.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 24° C., night temperatures about 19° C., and light levels about 4,000 foot-candles. Single plants were grown in 16.5-cm pots, pinched one time, and flowered under naturally lengthening nyctoperiods during the fall. Plants used for the description were about 18 weeks old.

In the following description, color references are made to The Royal Horticultural Society Colour Chart except where general terms of ordinary dictionary significance are used.

Botanical classification: *Euphorbia pulcherrima* Willd. cultivar Eckadin.

Parentage:

*Female parent.*—*Poinsettia pulcherrima* Willd. cultivar 603, disclosed in U.S. Plant Pat. No. 9,952.

*Male parent.*—Proprietary *Poinsetta pulcherrima* Willd. selection identified as F-14, not patented.

Propagation:

*Type cutting.*—Terminal cuttings.

*Time to initiate roots.*—About 10 days at 20 to 22° C.

*Time to develop roots.*—About 28 days at 20 to 22° C.

*Rooting habit.*—Thick, fibrous and freely-branching.

Plant description:

*Plant form.*—Inverted triangle, top of plant rounded; mounding.

*Growth habit.*—Upright, compact and uniform plant habit. Upright branch angle. Very freely branching; branching is enhanced by removing the shoot apex; about 8 to 9 lateral branches develop after removal of the terminal apex. Moderate vigor to vigorous.

*Plant height.*—About 30 cm.

*Plant diameter or spread.*—About 48 cm.

*Crop time.*—From unrooted cuttings to a flowering plant in a 16.5-cm container, about 18 weeks are required.

*Stem description.*—Lateral branch length: About 23 cm. Lateral branch diameter: About 1 cm. Internode length: About 1.75 cm. Stem color: 146A blushed with 60B.

*Foliage description.*—Alternate, simple. Quantity of leaves per lateral branch: About 8. Length: About 12.5 cm. Width: About 9.5 cm. Shape: Mostly ovate; occassionally lobed. Apex: Acuminate. Base: Rounded acute. Margin: Entire. Texture: Mostly glabrous with very slight pubescence on lower surface. Surface: Smooth, not rugose. Color: Young foliage, upper surface: Darker than 147A. Young foliage, lower surface: 147A. Mature foliage, upper surface: Much darker than 147A; venation, 145A. Mature foliage, lower surface: 147A; venation, 147C to 147D. Petiole: Length: About 4.8 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Response time, about 9 weeks; natural season flower maturity date is November 28 for plants grown in Encinitas, Calif.

*Post-production longevity.*—Plants of the new Poinsettia maintain good substance and bract color for about 4 to 6 weeks under interior conditions and for about 8 weeks under greenhouse conditions.

*Quantity of inflorescences.*—One per lateral branch, usually about 8 or 9 per plant.

*Inflorescence size.*—Diameter: About 35 cm. Height (depth): About 5.5 cm.

*Flower bracts.*—Quantity of flower bracts per inflorescence: Usually about 12 to 13 primary bracts and about 4 to 6 smaller secondary bracts per inflorescence. Length, largest bracts: About 18 cm; stalk about 3 cm. Width, largest bracts: About 10.5 cm. Shape: Mostly ovate. Apex: Acuminate. Base: Acute. Margin: Entire. Texture: Glabrous, velvety. Surface: Smooth, not rugose. Orientation: Mostly horizontal to slightly upright. Color: Developing, upper surface: 46A. Developing, lower surface: 46B. Mature, upper surface: 45A; color does not fade with subsequent development. Mature, lower surface: 53C.

*Cyathia.*—Quantity: Usually about 9 to 10 per corymb. Diameter of cyathia cluster: About 3 by 3 cm. Length: About 1 cm. Width: About 7 mm. Shape: Oval. Color: Immature and mature, 144A. Peduncle: Length: About 5 mm. Aspect: Strong, erect. Color: 144B. Stamens: Stamen number: Typically about 10 per cyathium. Anther shape: Oval. Anther length: About 1 mm. Anther color: 45A. Amount of pollen: Scarce. Pollen color: 9A. Pistils: Not observed. Nectary number: One per cyathia. Nectary color: 14A.

Disease resistance: Resistance to pathogens common to Poinsettias has not been observed on plants grown under commercial conditions.

It is claimed:

1. A new and distinct cultivar of Poinsettia plant named 'Eckadin', as illustrated and described.

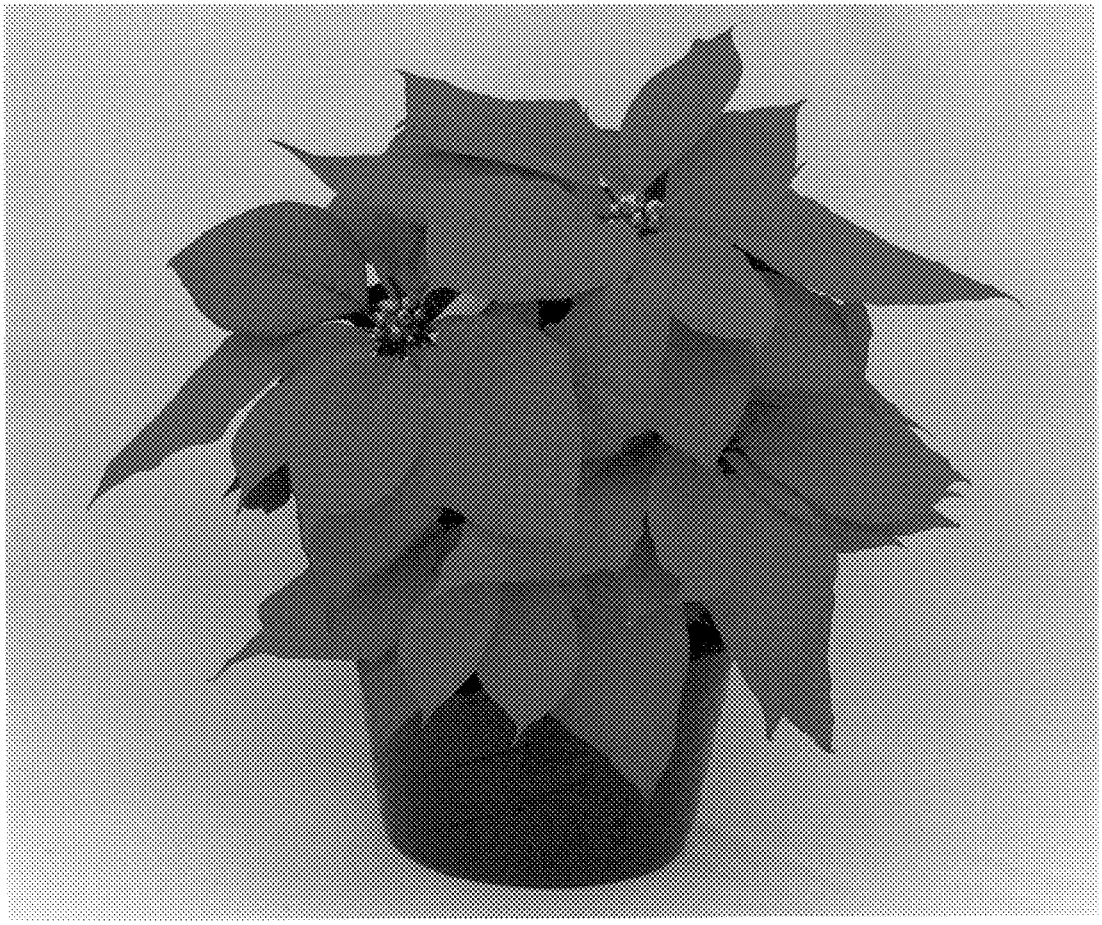

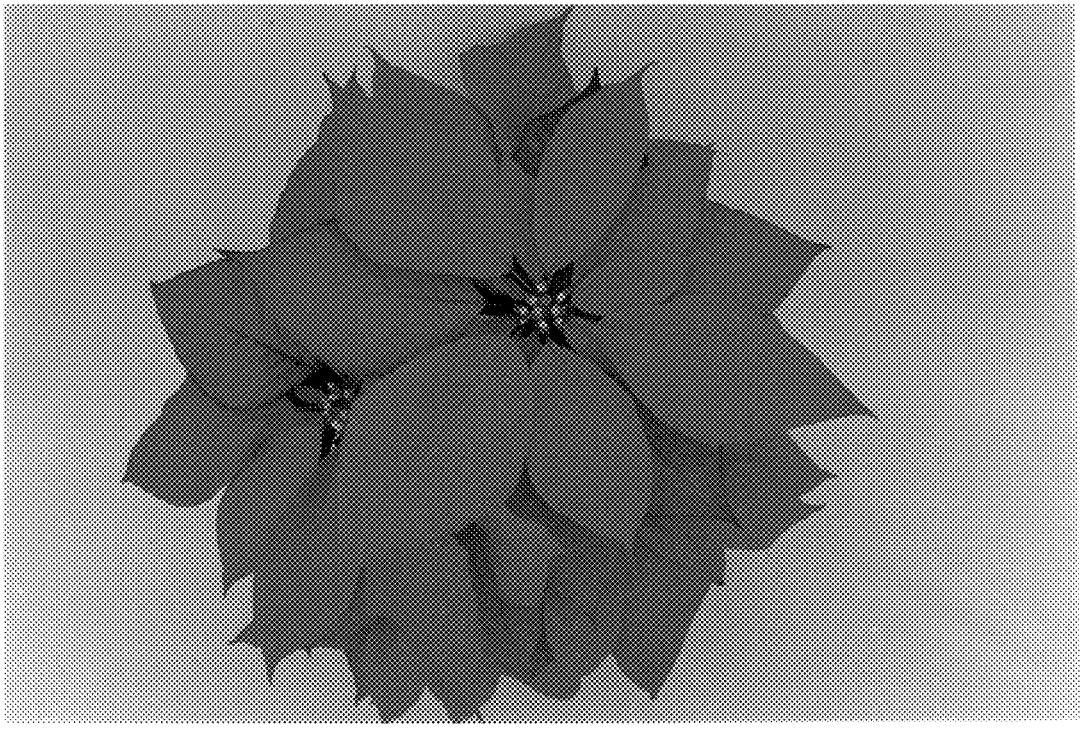
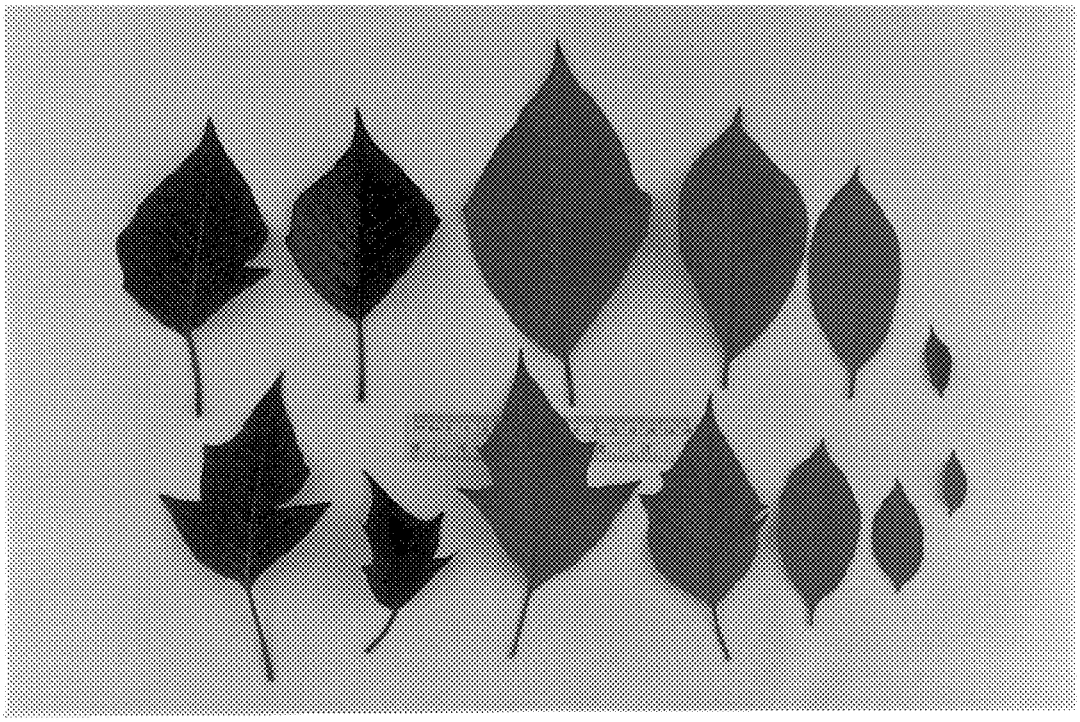

* * * * *